US00PP30983P2

(12) United States Plant Patent
Bregman

(10) Patent No.: US PP30,983 P2
(45) Date of Patent: Oct. 29, 2019

(54) ***HYDRANGEA* PLANT NAMED 'AJ14'**

(50) Latin Name: *Hydrangea paniculata*
Varietal Denomination: AJ14

(71) Applicant: Arie Jacobus Bregman, Benthuizen (NL)

(72) Inventor: Arie Jacobus Bregman, Benthuizen (NL)

( * ) Notice: Subject to any disclaimer, the term of this patent is extended or adjusted under 35 U.S.C. 154(b) by 0 days.

(21) Appl. No.: 16/350,221

(22) Filed: Oct. 15, 2018

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Barbara Campbell; Cochran Freund & Young LLC

(57) ABSTRACT

A new *hydrangea* plant particularly distinguished by having large white inflorescences and a broad obovate to near globular plant shape, is disclosed.

2 Drawing Sheets

Genus and species: *Hydrangea paniculata.*
Variety denomination: 'AJ14'.

BACKGROUND OF THE NEW PLANT

The present invention comprises a new and distinct variety of *hydrangea* plant, botanically known as *Hydrangea paniculata*, and hereinafter referred to by the variety name 'AJ14'. 'AJ14' originated from an open pollination in The Netherlands using the female *Hydrangea paniculata* parent 'Dharuma' (unpatented) and un-named and unpatented *Hydrangea paniculata* male parents. Seeds from the open-pollination were taken from the female parent and sown and a single plant was chosen in 2008.

'AJ14' was first propagated in June 2013 in The Netherlands. 'AJ14' was found to reproduce true to type in successive generations of asexual propagation via softwood cuttings.

SUMMARY

The following are the most outstanding and distinguishing characteristics of this new variety when grown under normal horticultural practices in Kaatsheuvel, The Netherlands.

1. Large white inflorescences; and
2. A broad obovate to near globular plant shape.

DESCRIPTION OF THE PHOTOGRAPHS

This new *hydrangea* plant is illustrated by the accompanying photographs which shows the plant's overall plant habit including form, and foliage. The photographs are of a 3-liter container. Photos were taken in June 2018 in Boskoop, The Netherlands. The colors shown are as true as can be reasonably obtained by conventional photographic procedures.

Figure 1:
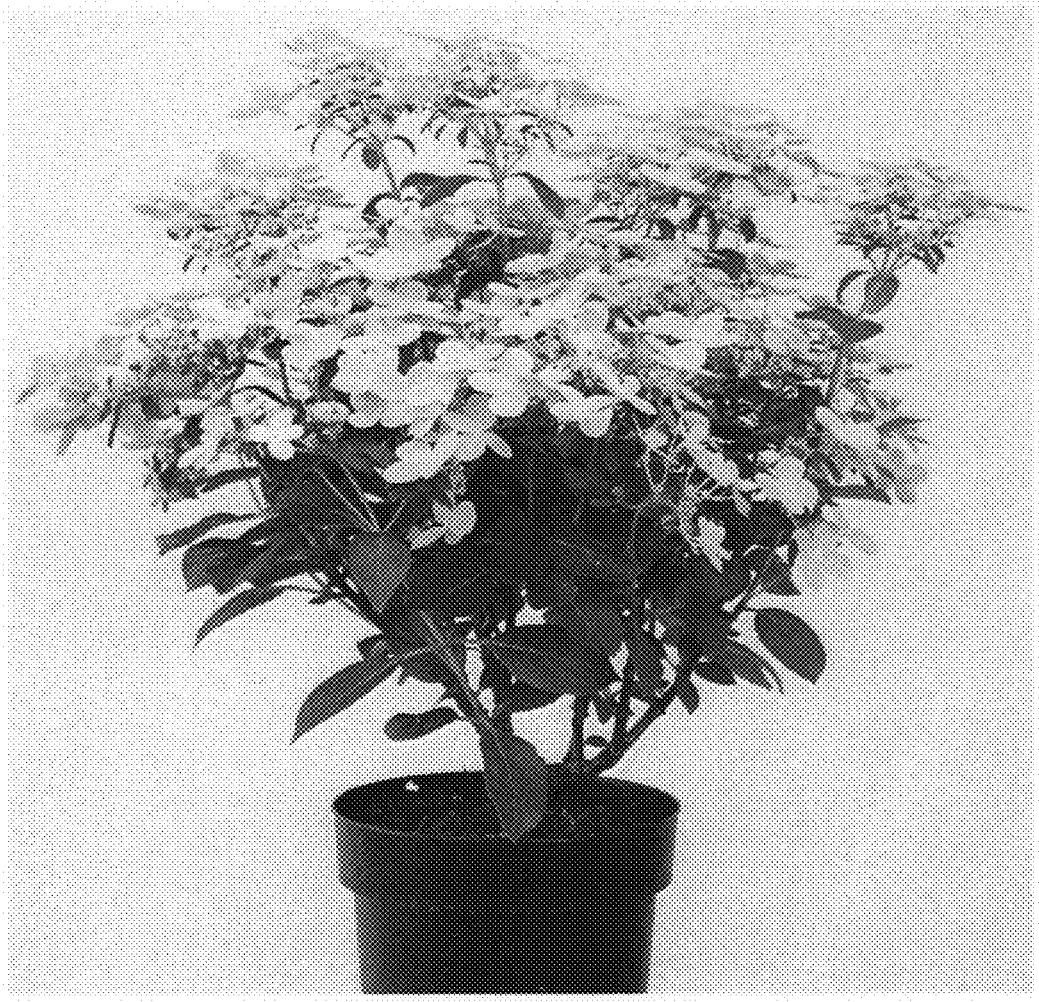
Figure 2:
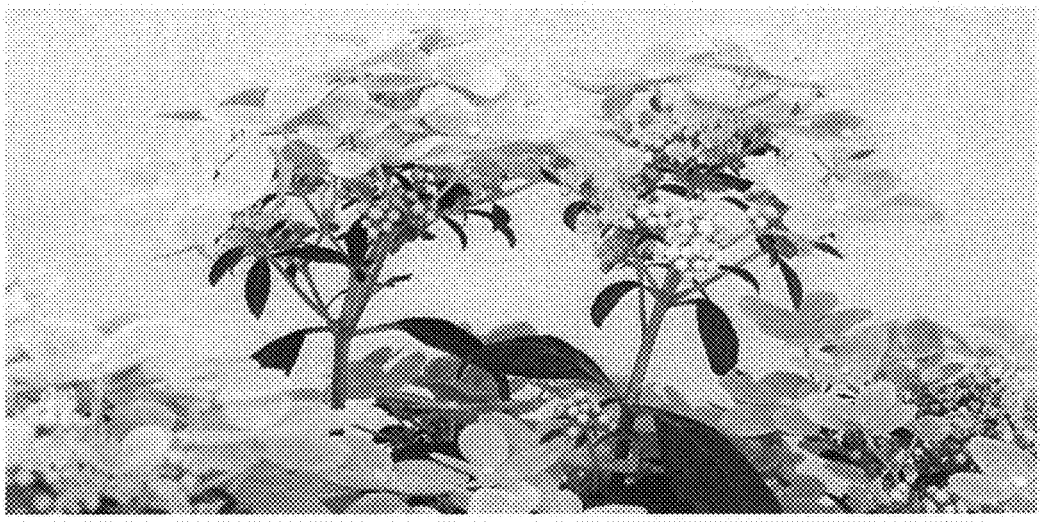
Figure 3:
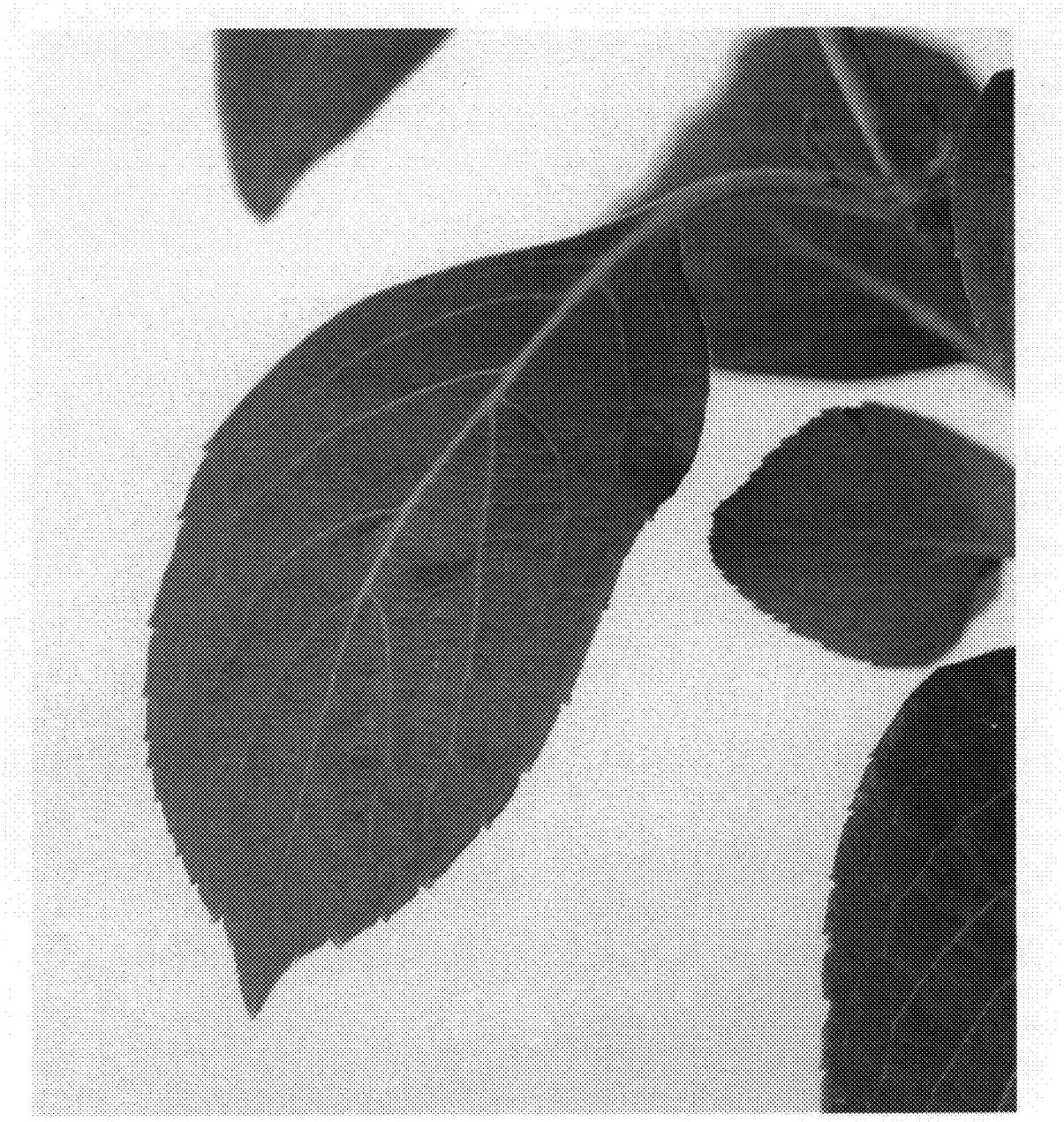

FIG. 1 shows the overall plant habit of 'AJ14'.
FIG. 2 shows a close-up of the flowers.
FIG. 3 shows a close-up of the foliage.

DESCRIPTION OF THE NEW VARIETY

The following detailed descriptions set forth the distinctive characteristics of 'AJ14'. The data which define these characteristics were collected from asexual reproductions carried out in Kaatsheuvel, The Netherlands. Data was collected on two-year old plants grown outdoors in a 19 cm circular pot The Netherlands in June 2018. The range of day temperatures was 16° C. to 30° C. and the range of night temperatures was 10° C. to 18° C. Color references are to The R.H.S. Colour Chart of The Royal Horticultural Society of London (R.H.S.), $6^{th}$ edition (2015).

Classification:
- *Family.*—Hydrangeaceae.
- *Botanical.*—*Hydrangea paniculata.*
- *Common.*—*Hydrangea.*
- *Designation.*—'AJ14'.

Plant:
- *Propagation type.*—Softwood.
- *Time to produce a finished plant.*—Average is one year from propagation to a small finished plant.
- *Plant shape.*—Broad obovate to near globular.
- *Average plant height.*—43.7 cm.
- *Average plant diameter.*—51.5 cm.
- *Growth rate.*—Low to moderate.
- *Vigor.*—Moderate.
- *High temperature tolerance.*—At least tolerant to USDA Zone 9.
- *Low temperature tolerance.*—At least tolerant to USDA Zone 5.
- *Weather tolerances.*—Moderate tolerance to wind; moderate to high tolerance to rain.
- *Disease/pest resistance and susceptibility.*—Not more susceptible to pests and diseases than other varieties of same species.

Branches:
- *Habit.*—Freely branching, bushy.
- *Basal branching.*—Present.
- *Pinching.*—Not required but will improve branching.

*Lateral branches*.—Number of lateral branches per plant: Average of 22. Length: Average is 18.3 cm, excluding inflorescence. Diameter: Average is 0.35 cm. Internode length: Average is 7.5 cm. Appearance and shape: Rounded. Aspect/angle: Upright; average angle of 40 degrees to main branch. Strength: Strong.

*Color, immature*.—RHS 148C (Yellow-green) with RHS 193B (Greyed-green lenticels).

*Color, mature*.—RHS 148D (Yellow-green) fading to RHS 199A (Greyed-brown) when maturing; older bark is RHS 200B to RHS 200D (Brown).

*Pubescence*.—Immature stems are very sparsely covered with short adpressed hairs, average length 0.02 cm, white in color, but too small and sparse to be measured with R.H.S. color chart.

*Lenticels*.—Stems are moderately covered with small lenticels, average length of 0.15 cm and average diameter of 0.03 cm and RHS 192C (Greyed-green).

Foliage:

*General*.—

*Arrangement*.—Opposite.

*Number of leaves per lateral branch*.—Approximately 12.

*Shape*.—Broad ovate.

*Apex*.—Short apiculate.

*Base*.—Short attenuate.

*Margin*.—Serrate.

*Length*.—Average is 7.0 cm.

*Width*.—Average is 4.2 cm.

*Texture*.—Upper surface is smooth, glabrous, and slightly glossy; lower surface is matte.

*Pubescence*.—No leaf pubescence except for very short pubescence on lower surface that is sparsely present, average length of 0.1 cm, and colored green-white but too small to be measured with R.H.S. color chart.

*Venation pattern*.—Pinnate.

*Venation color*.—Upper surface: RHS 146C to RHS 146D (Yellow-green). Lower surface: RHS 146D (Yellow-green).

*Color*.—Immature: Upper surface: Between RHS 139A (Green). Lower surface: Between RHS 147B (Yellow-green). Mature: Upper surface: RHS NN137A (Green). Lower surface: Starts at RHS 147B (Yellow-green) and turns to RHS 191A (Greyed-green).

*Petiole*.—Length: Average is 2.1 cm. Diameter: Flattened, average is 0.3 cm at widest part, 0.2 cm at widest part. Color: Upper surface is RHS 152B (Yellow-green) with RHS 174A (Greyed-green) margins and lower surface is RHS 146D (Yellow-green) and RHS 177C to RHS 177D (Greyed-orange) margins. Texture: Upper surface: Smooth, glabrous, except for on margins which are sparsely covered with very short hairs with an average length of 0.05 cm and colored green-white and too small to be measured by R.H.S. color chart. Lower surface: Smooth, glabrous, and very slightly glossy.

*Durability of foliage to stresses*.—High.

Flowers:

*Natural flowering season*.—Early summer to late summer.

*Fragrance*.—Moderately strong, sweet and pleasant.

*General*.—Terminal compound flattened corymb comprised of a center region of fertile florets surrounded by an outer ring of sterile florets; corymb is 8.4 cm in height and 12.9 cm in diameter.

*Sterile florets bud*.—Average length is 0.7 cm and average diameter is 1.3 cm; shape is cup-shaped and color is RHS 145C (Yellow-green).

*Fertile florets bud*.—Average length is 0.35 cm and average diameter is 0.25 cm; shape is obovate and color is RHS 157B (Green-white); immature calyx is between RHS 148D (Yellow-green) to RHS 157A (Green-white).

*Sterile florets*.—Average of 18 (range of 8 to 24) of sterile florets per inflorescence; aspect is slightly upright to slightly outward; shape is rotate; average diameter is 4.4 cm; average depth is 0.6 cm; longevity of florets on plant is about 6 weeks; florets are persistent; average of 4 petals per floret; petals are rotate in arrangement; petal shape is ovate, strongly concave; petal apex is acute; petal base is cuneate; petal margin is entire; petal average length is 0.2 cm; petal average width is 0.1 cm; petal upper surface is glabrous and slightly glossy; petal lower surface is glabrous and matte; floret color when opening and fully opened is RHS NN155B (both upper and lower surfaces); flowers do not fade but drop when they mature; average number of 4 sepals per floret but sometimes 3; sepal arrangement is rotate (cruciform); sepal shape is ovate to broad ovate; sepal apex is obtuse to broad and not deeply emarginate; sepal base is cuneate; sepal margin is entire, non-undulate; sepal length is 2.1 cm; sepal width is 1.2 cm; sepal texture (both surfaces) is glabrous and matte; sepal upper surface color is RHS 145B (Yellow-green) and sepal lower surface color is RHS 145C (Yellow-green); sepal color upper surface fully-opened is RHS 145B (Yellow-green) and sepal color lower surface fully-opened is between RHS 145B (Yellow-green) and RHS 145C (Yellow-green); pedicel length is 2.1 cm; pedicel diameter is 0.1 cm; pedicel angle is average of 45 degrees to main peduncle; pedicel strength is strong; pedicel texture is matte and densely covered with thin pubescence, average length of hairs is shorter than 0.03 cm and RHS 157B (Green-white); androecium present; average of 8 stamens; filament length is 0.1 cm; filament color is RHS NN155A (White); anther shape is double broad oblong; anther length is 0.1 cm; anther color is RHS 160D (Greyed-yellow); pollen amount is low; pollen color is RHS 158D (Yellow-white); Gynoecium present; average of 1 pistil per floret; pistil length is 0.15 cm; stigma shape is club-shaped; stigma color is RHS NN155D (White); style length is 0.1 cm; style color is RHS 157D (Green-white); ovary color is RHS 150D (Yellow-green).

*Fertile florets*.—Average of 280 per inflorescence; floret aspect is upright to outward; floret shape is rotate and florets drop when mature; floret diameter is 0.6 cm; floret depth is 0.4 mm; floret longevity on the plant is 5 days; flowers are self-cleaning; 5 petals per flower; petal arrangement is rotate; petal shape is ovate and concave; petal tip is acute; petal base is cuneate; petal margin is entire; petal length is 0.3 cm; petal width is 0.2 cm; petal texture is glabrous and matte for both upper and lower surfaces; petal color is RHS NN155B (White) for both upper and lower surfaces when opening and when fully-opened; petal color does not fade when mature but petals drop; average of 5 sepals per floret; sepal arrangement is rotate; sepal shape is deltoid; sepal tip is broad acute; sepal base is broad cuneate; sepal margin is entire; sepal length is 0.1 cm; sepal width is 0.125 cm; sepal texture (both surfaces) is glabrous and matte; sepal color for both upper and lower surfaces and when opened and fully opened is RHS 145D (Yellow-green) and the tip is RHS 145D (Greyed-purple); sepals do not fade with maturity; pedicel length is 0.35 cm; pedicel diameter is 0.1 cm; pedicel angle is 20 degrees to the peduncle; pedicel strength is moderate; pedicel texture is matte and densely covered with thin pubescence with an average length of 0.02 cm and RHS 157B (Green-white); pedicel color is RHS 145D (Yellow-white); stamen number is 8; filament length is 0.3 cm; filament color is RHS NN155D (White); anther shape is double broad oblong; anther length is 0.08 cm; anther color is RHS 160D (Greyed-yellow); amount of pollen of low; pollen color is RHS 158D (Yellow-white); average number of pistils per floret is 3; pistil length is 0.2 cm; stigma shape is club-shaped; stigma color is RHS 157C to RHS 157D (Green-white); style length is 0.1 cm; style color is RHS 145C (Yellow-green); ovary color is RHS 145C (Yellow-green).

*Seed*.—Not observed.

COMPARISON WITH PARENTAL AND COMMERCIAL VARIETIES

'AJ14' can be distinguished between the female *Hydrangea paniculata* parent 'Dharuma' (unpatented) in that the mature flowers of 'Dharuma' fades to a white and pink color at maturity, while the flower color of 'AJ14' is white and does not fade in color at maturity.

'AJ14' can be distinguished between the commercial variety 'Hort 09-012-05' (U.S. Plant Pat. No. 29,447) in Table 1.

TABLE 1

Comparison with Commercial Variety

| Characteristic | 'AJ14' | 'Hort 09-012-05' |
|---|---|---|
| Number of sterile flowers per inflorescence | 18 | 44 |
| Number of fertile flowers per inflorescence | 280 | 280 |

I claim:

1. A new and distinct variety of *Hydrangea* plant designated 'AJ14' as illustrated and described herein.

* * * * *